(12) United States Patent
Rost

(10) Patent No.: US 10,342,460 B2
(45) Date of Patent: Jul. 9, 2019

(54) POSTURAL FEEDBACK DEVICE

(71) Applicant: REHAB TECHNOLOGIES, LLC, Redmond, OR (US)

(72) Inventor: Brian Mitchell Rost, Redmond, OR (US)

(73) Assignee: REHAB TECHNOLOGIES, LLC, Redmond, OR (US)

( * ) Notice: Subject to any disclaimer, the term of this patent is extended or adjusted under 35 U.S.C. 154(b) by 396 days.

(21) Appl. No.: 15/170,829

(22) Filed: Jun. 1, 2016

(65) Prior Publication Data

US 2016/0345868 A1 Dec. 1, 2016

Related U.S. Application Data

(60) Provisional application No. 62/169,126, filed on Jun. 1, 2015.

(51) Int. Cl.
*A61B 5/00* (2006.01)
*A61B 5/11* (2006.01)
*A61B 5/107* (2006.01)

(52) U.S. Cl.
CPC .......... *A61B 5/1116* (2013.01); *A61B 5/1071* (2013.01); *A61B 5/1072* (2013.01);
(Continued)

(58) Field of Classification Search
CPC ......... A61B 5/11; A61B 5/1116; A61B 5/103; A61B 5/486; A61B 5/1072; A61B 5/4561; A61B 5/4566
See application file for complete search history.

(56) References Cited

U.S. PATENT DOCUMENTS 4,617,525 A 10/1986 Lloyd
5,038,137 A 8/1991 Lloyd
(Continued)

OTHER PUBLICATIONS

Saggio, G., "Bend sensor arrays for hand movement tracking in biomedical systems," 4th IEEE International Workshop on Advances in Sensors and Interfaces (IWASI 2011), Jun. 28, 2011, Savelletri di Fasano, (Brindisi), Italy, 3 pages.
(Continued)

*Primary Examiner* — Max F Hindenburg
(74) *Attorney, Agent, or Firm* — McCoy Russell LLP

(57) ABSTRACT

A postural feedback device for assisting user awareness of joint, muscle, or body part alignment is disclosed. Embodiments include at least one linear or rotary sensing unit comfortably and discretely adhered to the user's skin, a hardwire connection cable or wireless transmission sending unit, and an electronic console for interpretation of information from the sensing unit and biofeedback of said information via stimulus to the user. The postural feedback device may comprise multiple sensing units of various sizes simultaneously allowing for variations in application, user size, and size of body part being monitored. The electronic console may provide biofeedback to the user in the form of tactile, auditory, visual, or other stimuli, aiding the user in awareness of postural alignment or instruction of a desired anatomical movement. The sensing unit may be constructed allowing a low-profile, comfortable fit, allowing the device to be worn discreetly underneath clothing.

20 Claims, 7 Drawing Sheets

(52) U.S. Cl.
CPC ............ *A61B 5/4561* (2013.01); *A61B 5/486* (2013.01); *A61B 5/6804* (2013.01); *A61B 5/6833* (2013.01); *A61B 5/742* (2013.01); *A61B 5/7405* (2013.01); *A61B 5/7455* (2013.01); *A61B 2503/10* (2013.01)

(56) References Cited

U.S. PATENT DOCUMENTS

| | | | |
|---|---|---|---|
| 5,168,264 A | 12/1992 | Agustin | |
| 5,469,831 A | 11/1995 | Piscopo et al. | |
| 6,487,906 B1 * | 12/2002 | Hock | A61B 5/1126 73/379.01 |
| 7,070,571 B2 * | 7/2006 | Kramer | A61B 5/1071 600/595 |
| 7,431,703 B2 * | 10/2008 | Salvi | A61B 5/1121 600/594 |
| 7,471,290 B2 | 12/2008 | Wang et al. | |
| 7,848,811 B2 | 12/2010 | Moon et al. | |
| 8,165,840 B2 | 4/2012 | Hatlestad et al. | |
| 8,768,430 B2 | 7/2014 | Doerr et al. | |
| 8,784,323 B2 | 7/2014 | Nabutovsky et al. | |
| 8,818,748 B2 | 8/2014 | Hatlestad et al. | |
| D715,667 S | 10/2014 | Shigeno et al. | |
| 8,868,373 B2 * | 10/2014 | Eng | A61F 4/00 128/899 |
| 8,928,484 B2 | 1/2015 | Chang et al. | |
| 9,173,596 B1 * | 11/2015 | Berme | G06F 19/3481 |
| 9,799,187 B2 * | 10/2017 | Limonadi | A61B 5/6831 |
| 9,804,189 B2 * | 10/2017 | Takenaka | G01P 15/18 |
| 9,936,921 B2 * | 4/2018 | Pettit | A61B 5/7275 |
| 2008/0100459 A1 | 5/2008 | Hoffman et al. | |
| 2010/0010383 A1 | 1/2010 | Skelton et al. | |
| 2013/0207889 A1 | 8/2013 | Chang et al. | |
| 2014/0364769 A1 | 12/2014 | Chang et al. | |

OTHER PUBLICATIONS

"Lumo Lift—Posture Coach & Activity Tracker," Lumo Body Tech Website, Available Online at http://www.lumobodytech.com/lumo-lift/, Available as Early as Sep. 9, 2015, 19 pages.

* cited by examiner

POSTURAL FEEDBACK DEVICE

CROSS-REFERENCE TO RELATED APPLICATIONS

The present application claims priority to U.S. Provisional Patent Application No. 62/169,126, entitled "POSTURAL FEEDBACK DEVICE," filed on Jun. 1, 2015, the entire contents of which are hereby incorporated by reference for all purposes.

BACKGROUND/SUMMARY

It is known that poor posture may lead to health complications such as back pain. Back pain however may be addressed by maintaining good posture such as a "neutral spine position" while sitting, standing, lying or moving. The neutral spine position in a healthy spine is a position in which three natural curves of the spine, cervical, thoracic, and lumbar regions maintain their natural curves. The cervical region curve involves cervical vertebrae C1-C7 and is naturally anteriorly convex. The thoracic region curve involves thoracic vertebrae T1-T12 and is naturally posteriorly convex. The lumbar region curve involves lumbar vertebrae L1-L5 and is naturally anteriorly convex.

Conventional methods for providing postural feedback to a user typically require special garments or belts to secure sensors in place and may require a user to carry a separate electronic console which supplies the postural feedback. With conventional methods, it may be difficult to apply such devices in a way that is visually appealing, comfortable, convenient, and effective. Additionally, conventional postural feedback devices may comprise an electronic console which may be bulky and may detract from the convenience of the unit. Further, such devices tend to be bulky and/or inflexible which may be uncomfortable to a user. Therefore, a postural feedback device that may be applied to a user onto skin or into garments worn by a user which communicates to an existing electronic console such as a mobile phone for example, may be beneficial to a user.

The present disclosure relates to a postural feedback device that can be used for measuring joint or muscle alignment of the human or animal body, or retraining a desired bodily position. The device may comprise at least two main components: 1) a sensing unit affixed to the skin or worn in a garment over a desired joint, multiple joints, or body part that may measure changes in the distance between at least two points that may measure both linear and/or curvilinear changes in the distance between at least two points, and 2) a battery or solar powered electronic console connected to a regulator such as a potentiometer or capacitor via hardwire or remote signal, for the analysis and display of the sensing unit readings. The electronic console may be in the form of a pager, cell phone, electronic bracelet, wristwatch or other suitable electronic device that may be configured to provide feedback to the user through auditory, visual, tactile, or other sensory stimuli for the purpose of general knowledge or to encourage a given movement or postural behavior. Further, as a non-limiting example, the electronic console may be incorporated internally into the hardware of the sensing unit. The sensing unit may comprise a plurality of various sizes and/or shapes to accommodate various sized users and body parts, and be worn discreetly underneath clothing if so desired.

The present disclosure relates to a postural feedback device that may measure the linear and/or curvilinear excursion between two points, as measured by a sensing unit, to provide knowledge and training of human or animal joint, muscle, or other body part alignment. The posture measuring device may comprise at least one regulator that may be secured to the body at two non-moveable points and an electronic console in the form of a pager, a cell phone, a portable computing device, a tablet PC, a personal digital assistant (PDA), a smart watch, a wearable computing device, a computing device, or other equivalent electronic device that may be connected either directly via hardwire for example, or remotely via a wireless signal, to the regulator for interpretation, display, and feedback purposes. Further, the electronic console may be able to provide feedback to a user through auditory, visual, tactile, or alternate stimuli to assist the user in general awareness or the retraining of a desired movement or position. The device may further comprise multiple or various sized sensing units to fit various applications and differently sized body parts and users, and may be worn discreetly under clothing.

In one embodiment, a regulator of the postural feedback device may comprise a centralized linear regulator with two fixated ends that may be utilized to measure postural alignment by measuring the linear and/or curvilinear change in distance between to the two fixated ends while still maintaining a thin profile such that the postural feedback device may be worn discreetly underneath clothing, or incorporated into an article of clothing. The information from the potentiometer may be transmitted to an electronic device via a hardwire connection or a wireless signal to provide feedback to the user.

In further embodiments, a postural feedback device may comprise a centralized rotary regulator which may be positioned between the two fixated ends to measure postural alignment by measuring the linear and/or curvilinear change in distance between the two fixated ends.

Additional embodiments of a postural feedback device may comprise one or more regulators configured to measure postural alignment by measuring the linear and/or curvilinear change in distance between the two fixated ends.

As a non-limiting example, embodiments of a postural feedback device may be provided within the scope of the present disclosure that comprise any type of regulator that may be configured to measure postural alignment by measuring the linear and/or curvilinear distance between the two fixated ends of the device.

As another non-limiting embodiment, a postural feedback device may comprise an electric console that may either be incorporated internally into the hardware of the regulator, or housed externally. The electric console may be configured to provide power to the regulator of the postural feedback device and may further provide visual, auditory, tactile, other alternate stimuli, or a combination thereof to assist the user with postural feedback.

In another embodiment, a postural feedback device may be compatible with various electronic devices such as mobile phones, watches, or other electronic devices that may provide feedback to the user via visual, auditory, tactile, or other alternate stimuli to assist the user with postural feedback.

In a further embodiment, the postural feedback device may comprise various sizes and materials that may be dependable, inexpensive, and effective in accomplishing the intended purposes of the postural feedback device.

This summary is provided to introduce a concept in simplified form that is further described below in the Detailed Description. This summary is not intended to identify key features of the claimed subject matter, nor is it intended to be used to limit the scope of the claimed subject matter. Furthermore the claimed subject matter is not limited to implementations that solve any or all disadvantages noted in any part of this disclosure.

DETAILED DESCRIPTION

The present disclosure relates to a postural feedback device designed to both educate and train a user to variations in body and/or joint alignment. The device may comprise at least one sensing unit to measure linear or curvilinear changes in joint, muscle, or body part alignment, and an electronic console in the form of a pager, cell phone, wrist watch, bracelet, or equivalent electronic device for the purposes of interpretation, display, and feedback of the regulator readings. The feedback may be auditory, visual, tactile, or any other form of stimulus effective to provide a user with knowledge for general awareness or retraining of bodily posture or behavior. Further, the sensing unit and electronic console may communicate either via direct hardwiring or remote signal. As a non-limiting example, the sensing unit may comprise a sliding sensing unit and may further comprise various shapes and sizes, with various levels of excursion, to accommodate variations in joint and user size. Further, the sensing unit may be removably attached to the user via adhesion, strapping, or within a garment, and be thin enough to be worn discreetly underneath clothing. Additionally, more than one sensing unit may be used to in certain applications where multiple joints or muscles may be monitored simultaneously.

Figure 1:
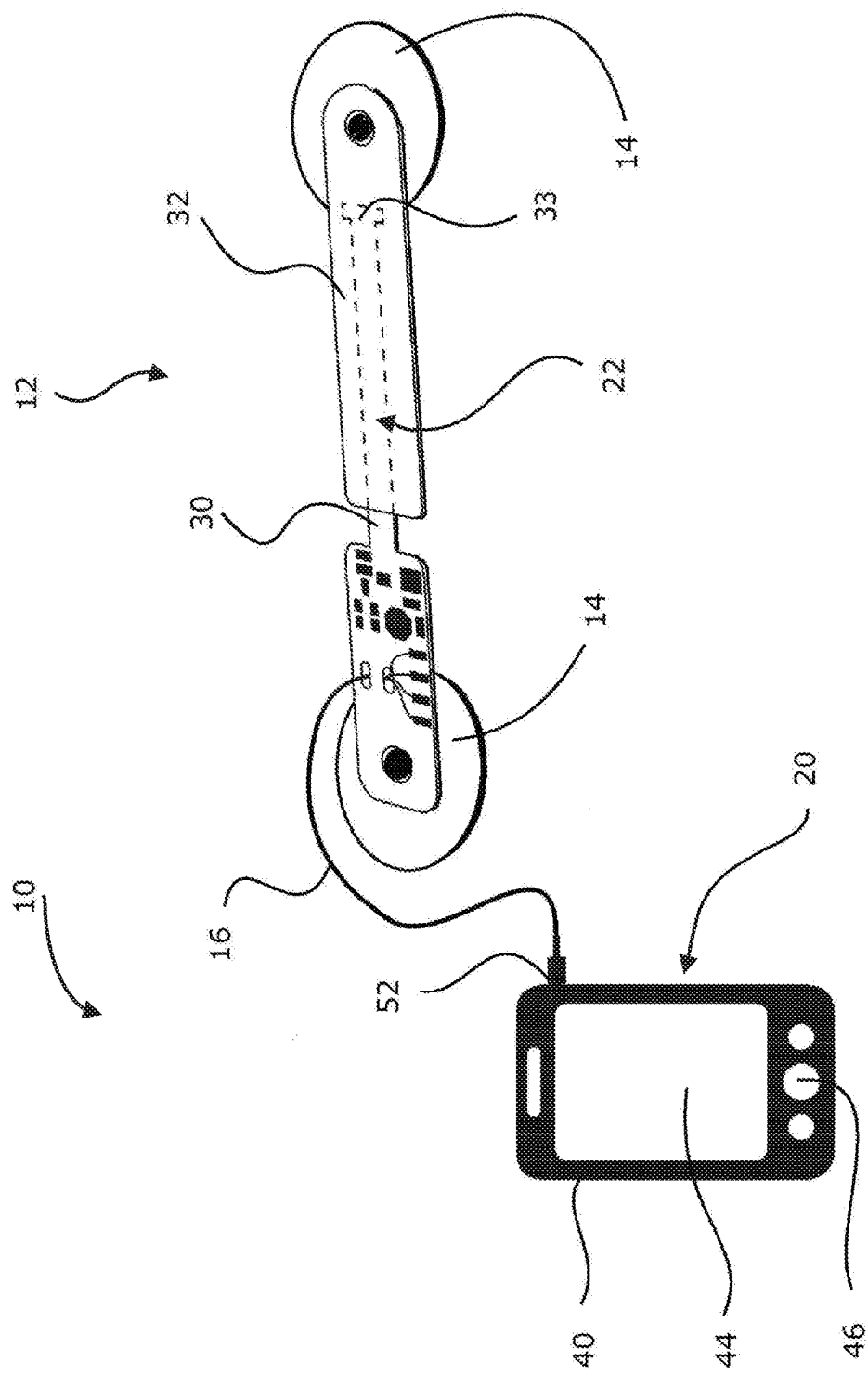
FIG. 1 illustrates a perspective view of a postural feedback device with sensing unit, a hardwire connection cable, and electronic console according to one embodiment of the present disclosure.
Figure 4:
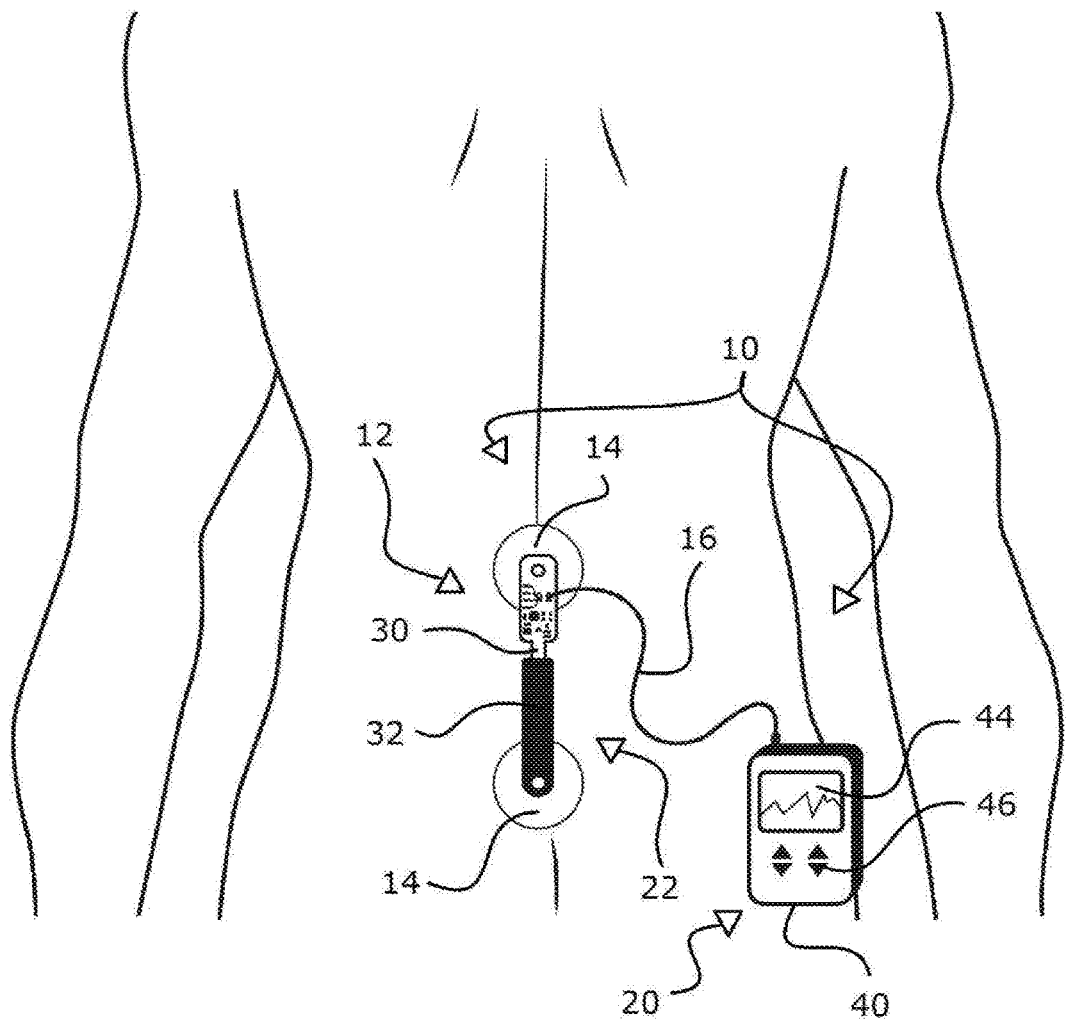
FIG. 4 illustrates a perspective view of a postural feedback device with a linear sensing unit, a hardwire connection cable, and electric console applied to a human back according to one embodiment of the present disclosure.
Figure 5:
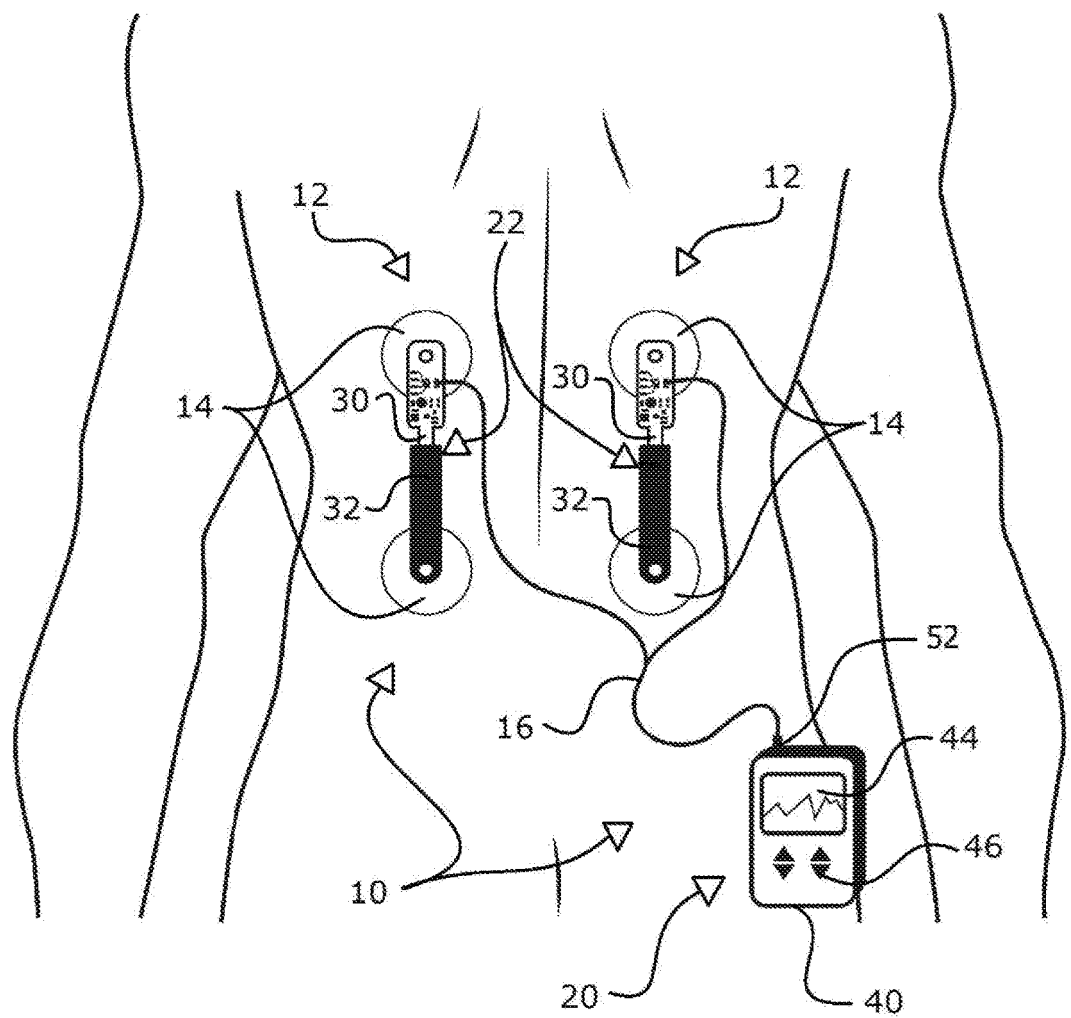
FIG. 5 illustrates a perspective view of a postural feedback device with dual linear sensing units, a hardwire connection cable, and electronic console applied to a human back according to one embodiment of the present disclosure.
Figure 6:
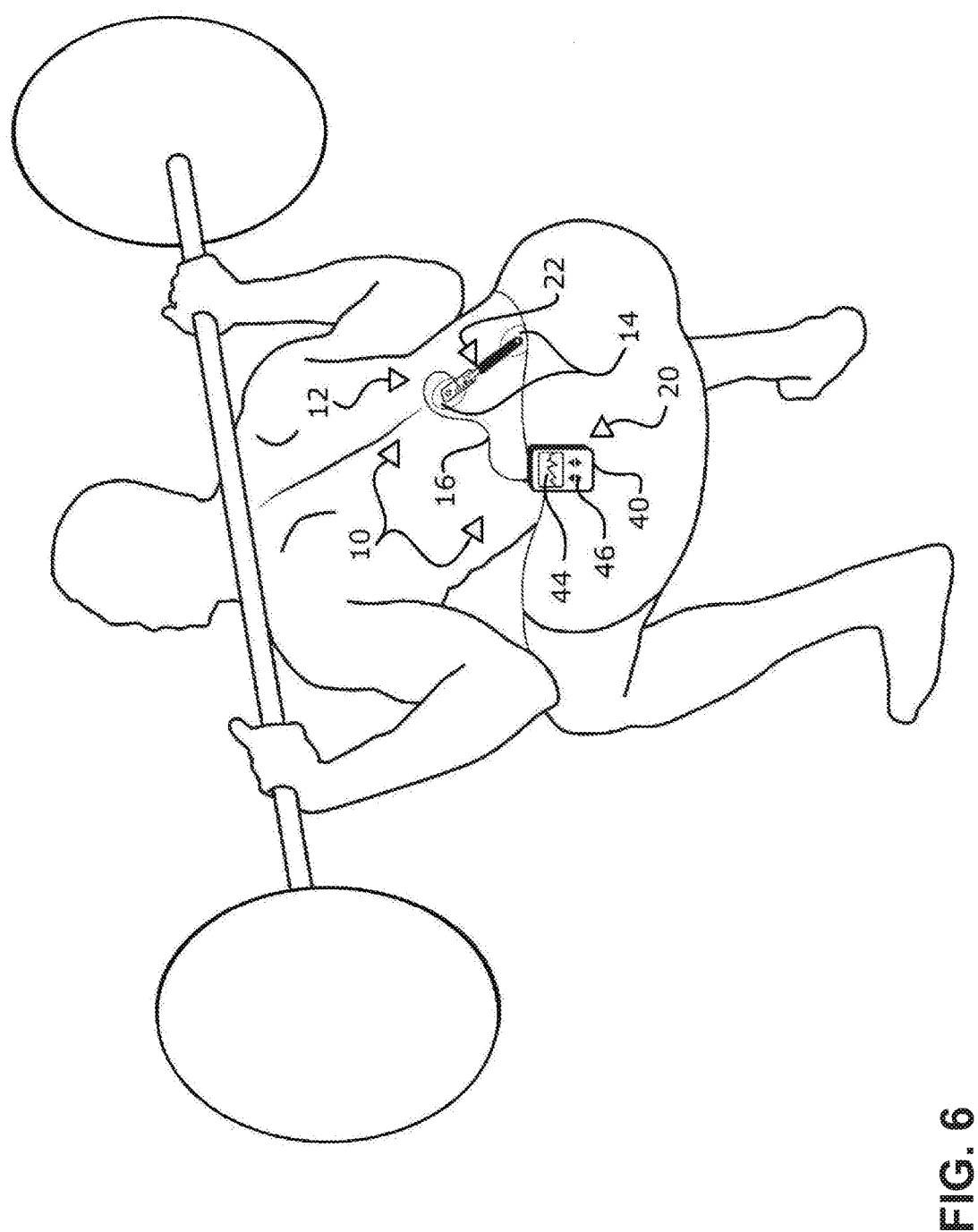
FIG. 6 illustrates a perspective view of a postural feedback device with a linear sensing unit, a hardwire connection cable, and electronic console applied to the back of a human weightlifter according to one embodiment of the present disclosure.

Turning to FIG. 1, an example of one embodiment of the postural feedback device 10 is shown. The postural feedback device may comprise a sensing unit 12 with a centralized linear regulator 22 and fixated ends 14, a hardwire connection cable 16, and an electronic console 20. The fixated ends 14 of the sensing unit 12 may comprise an adhesive material that may secure said fixated ends 14 of the sensing unit 12 to the user. Fixated ends 14 may be secured to the body of a user at one or more points such as two points on the back of the user as illustrated in FIGS. 4, 5, and 6, traversing a joint, or secured to a body part which the user desires to monitor. A change in position of the body part may cause a change in an electrical gradient reading generated by the centralized linear regulator which may be proportional to the distance between fixated ends 14. Sensing unit 12 may transmit the electrical gradient reading to the electronic console 20. The hardwire electronic connection cable 16 may connect the sliding sensing unit 12 to the electronic console 20 via electrical wire for example, thus transmitting the electrical gradient reading from the centralized linear regulator 22 to the electronic console 20. The electronic console 20 may be programmed to interpret the positioning of the sensing unit 12 and provide feedback to the user via visual, auditory, tactile or other stimuli, or combinations of each.

As used herein, the term "regulator" may include a potentiometer, a linear potentiometer, a rotary potentiometer, a capacitor, or any suitable device for regulating electrical current within the postural feedback device.

Accordingly, in one embodiment, a regulator of the postural feedback device may comprise a centralized linear potentiometer with two fixated ends that may be utilized to measure postural alignment by measuring the linear and/or curvilinear change in distance between to the two fixated ends while still maintaining a thin profile such that the postural feedback device may be worn discreetly underneath clothing, or incorporated into an article of clothing. The information from the potentiometer may be transmitted to an electronic device via a hardwire connection or a wireless signal to provide feedback to the user.

In further embodiments, a postural feedback device may comprise a centralized rotary potentiometer which may be positioned between the two fixated ends to measure postural alignment by measuring the linear and/or curvilinear change in distance between the two fixated ends.

Additional embodiments of a postural feedback device may comprise one or more capacitors configured to measure postural alignment by measuring the linear and/or curvilinear change in distance between the two fixated ends.

As a non-limiting example, embodiments of a postural feedback device may be provided within the scope of the present disclosure that comprise any type of regulator that may be configured to measure postural alignment by measuring the linear and/or curvilinear distance between the two fixated ends of the device.

In some embodiments, postural feedback device 10 may be secured to a single point on the body, incorporated into a wearable garment, or secured to multiple points on the body as illustrated in FIG. 5.

In another embodiment, the change in body position may be transmitted from fixated end 14 to a rotary potentiometer for example, via one or more actuator arms.

Alternate embodiments of the postural feedback device 10 may include variations in the configuration and mechanism of the sensing unit 12 with fixated ends 14 and centralized linear regulator 22, the hardwire connection cable 16, and an electronic console 20 such as a cell phone, or other electronic device.

The sensing unit 12 may comprise various flexible, semi-rigid, or rigid materials including, but not limited to: fabric, paper, cardboard, foam, metal, elastic fabric, leather, plastic, rubberized material, carbon fiber or other material meeting the intended function of the embodiment. Further, the material of the sensing unit 12 may be layered or infused with various conductive or magnetic materials including metal, electrolytes, semi-conductors, plasmas, or other conductive, semi-conductive, or magnetic materials while still meeting the intended function of the embodiment. The sensing unit 12 may comprise combinations of the above said materials. The centralized linear regulator 22 may comprise various shapes and sizes including square, rectangular, oval, round, tubular, rod shaped etc., while still meeting the intended function of the embodiment. The fixated ends 14 of the sensing unit 12 may comprise various shapes and sizes including square, rectangular, oval, round, etc., and may be singular or multiple in number while still meeting the intended function of the embodiment. The fixated ends may comprise various materials and methods to create an adhering effect to the user including, but not limited to, glue, suction, wet or dry gel, strapping, incorporation into a garment, etc. As a non-limiting example, the sensing unit 12 may comprise two halves each containing one fixated end 14 and one portion of the centralized linear regulator 22. Alternatively, the sensing unit 12 may comprise separate pieces for the fixated ends 14 and centralized linear regulator 22 that may then be adhered together by adhesive materials, rivets, heat pressing, sewing, button snaps, Velcro, or other methods of adhesion.

Figure 2:
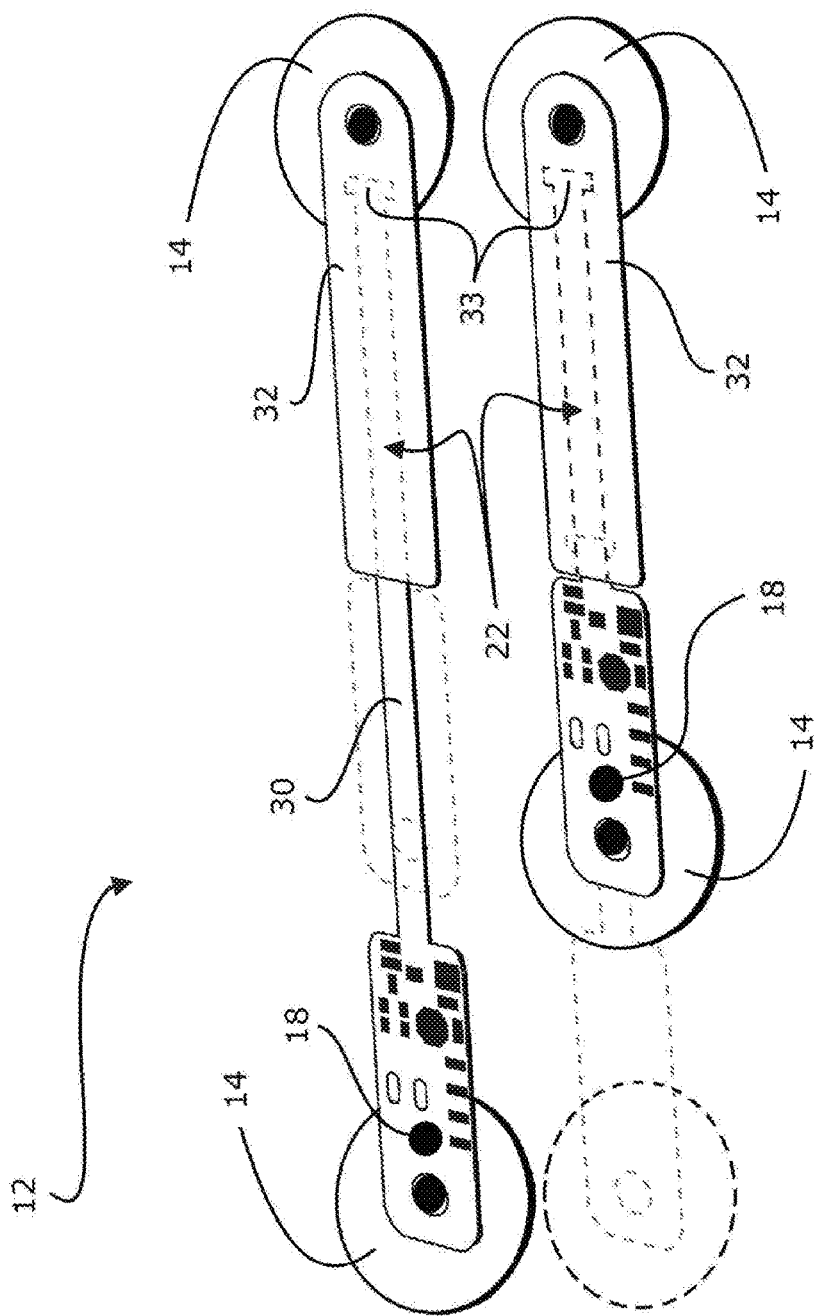
FIG. 2 illustrates a perspective view of a postural feedback device with dual linear sensing units according to one embodiment of the present disclosure.

The hardwire connection cable 16 may comprise various lengths, thicknesses, and conductive materials, while still meeting the intended purpose of the embodiment. The hardware connection cable 16 may comprise any material that effectively transmits an electrical current including, but not limited to, metal, electrolytes, semi-conductors, plasmas, or other conductive materials. Further, the hardware connection cable 16 may be replaced by a wireless transmission sending unit 18 on the sensing unit 12, as shown in FIG. 2. The wireless transmission sending unit may be configured to send or transmit a signal indicating an electrical gradient from the centralized regulator 22 to the electronic console 20. The hardwire connection cable 16 may be attached to the electronic console 20 such as a cell phone through a variety of modular jacks 52 including but not limited to, an earphone jack, mini RCA jack, USB port, HDMI port, or other similar port/jack. The hardwire connection cable 16 may comprise an attachment to the user or user's clothing including, but not limited to, a fixated patch, clips, Velcro, magnetic couplers, etc.

The electronic console 20 may be incorporated internally into the hardware of the sensing unit 12, or may alternatively comprise the equivalent of various electronic devices including, but not limited to: pagers, cell phones, wrist watches, bracelets, or other small electronic devices. The electronic console 20 may comprise various sizes and shapes including, but not limited to: square, rectangular, round, discoid, triangular, tubular, etc., while still meeting the intended purpose of the embodiment. Further, the electronic console 20 may be comprised of various shapes, materials, and textures to adjust grip or fit for the user. In one example embodiment as shown in FIG. 1, the electronic console 20 may resemble an electronic pager or cell phone with a plastic case 40 comprising internal circuitry, a display window 44, and control buttons 46. The plastic case 40 of the electronic console 20 may include an attachment mechanism to facilitate attachment of the electronic console to the user, an article of the user's clothing, or belt, including, but not limited to, a belt clip, waist strap, alligator clip, Velcro strap, etc. Further, the electronic console 20 may be placed in an external carrying case that may be attached to the user in a similar fashion as described above. The electronic console 20 may additionally be incorporated into an article of clothing including, but not limited to, a belt, wrist watch, belt buckle, bracelet, hat, etc. The electronic console 20 may comprise a display window 44 of various shapes and sizes while still meeting the intended function of the embodiment. The control buttons 46 of the electronic console 20 may be of various sizes and shapes including, but not limited to round, triangular, square, hexagonal, bulbous, flat, or other shape and/or combinations thereof. Further, the control buttons 46 may be of various textures such as smooth, rough, etc. It will be appreciated that the control buttons 46 may also be incorporated into the display window 44 wherein the display window 44 may comprise touchscreen technology. The internal circuitry of the electronic console 20 may comprise a vibratory mechanism, a speaker system, and/or a display window 44 to provide tactile, auditory, or visual feedback to the user. The electronic console 20 may comprise one or multiple connection jacks 52 for the attachment of hardwire connection cables 16 from one or more sensing units 12, earphones, and/or other accessories. The electronic console 20 may contain a mechanism for wireless communication with one or more sensing units 12, earphones, or other accessories. The electronic console 20 may be configured to be powered via battery, electric plug-in, solar mechanism, or another power source, while still meeting the intended function of the embodiment.

Turning to FIG. 2, a perspective view of one possible embodiment for the sensing unit 12 is depicted showing a possible sliding mechanism. The sensing unit 12 may comprise a centralized linear regulator 22 with an internal sliding member 30 and an external sliding member 32, a wireless transmission sending unit 18, and two fixated ends 14. The fixated ends 14 may comprise a variety of flexible, semi-rigid, or rigid materials and may further be coated with a variety of adhesive materials to secure said fixated ends 14 to the desired body part of a user. Alternatively, the fixated ends 14 of the sensing unit 12 may comprise straps, may be incorporated into a garment or may comprise any mechanism for securing said fixated ends 14 to the user. The centralized linear regulator 22 may be configured such that the internal sliding member 30 may fully traverse the external sliding member 32 in a telescoping manner which may allow for a change in distance between the two fixated ends 14. The centralized linear regulator 22 may traverse the fixated ends 14. Further, the centralized linear regulator 22 may comprise a barbed or bulbous end 33 disposed on the internal sliding member 30 that may prevent the internal sliding member 30 from exiting the external sliding member 32.

Alternate embodiments of the sensing unit 12 may include variations to the centralized linear regulator 22 with internal sliding member 30 and external sliding member 32, and fixated ends 14.

The centralized linear regulator 22 may comprise various lengths to accommodate differently sized users or body parts. The centralized linear regulator 22 may comprise a single internal sliding member 30 or multiple internal sliding members. The internal sliding member 30 may comprise a single material or combinations of non-rigid, semi-rigid or rigid materials including, but not limited to: plastic, paper, cardboard, foam, fabric, leather, metal, elastic fabric, rubberized material, carbon fiber, fiberglass, electrolytes, semi-conducting materials, conducting materials, plasmas, magnetic substances, or other materials while still meeting the intended function of the embodiment. The internal sliding member 30 may comprise various textures including, but not limited to smooth, dimpled, ridged, or grainy. The internal sliding member 30 may be of various shapes and including, but not limited to: rectangular, square, round, triangular, tubular, rod shaped, or combinations of shapes while still meeting the intended function of the embodiment. The internal sliding member 30 may comprise various color schemes, numbering sequences, or patterns to assist the user in measuring distance, applying the device correctly, and/or for aesthetics, etc. The internal sliding member 30 may traverse, or may be incorporated into the fixated ends 14. The centralized linear regulator 22 may comprise a centralized rotary regulator whereby the internal sliding member 30 and external sliding member 32 may be circular in shape and may be connected to the fixated ends 14 via actuating arms that may rotate the regulator surfaces while still meeting the intended function of the embodiment.

The centralized linear regulator 22 may comprise various lengths to accommodate differently sized users of body parts. The centralized linear regulator 22 may comprise a single external sliding member 32 or multiple internal sliding members. The external sliding member 32 may comprise a single material or combinations of non-rigid, semi-rigid or rigid materials including, but not limited to: plastic, paper, cardboard, foam, fabric, leather, metal, elastic fabric, rubberized material, carbon fiber, electrolytes, semi-conducting materials, conducting materials, plasmas, or other materials while still meeting the intended function of the embodiment. The external sliding member 32 may comprise various textures including, but not limited to smooth, dimpled, ridged, grainy, etc. The external sliding member 32 may be of various shapes including, but not limited to: rectangular, square, round, triangular, or combinations of shapes while still meeting the intended function of the embodiment. The external sliding member 32 may comprise various color schemes, numbering sequences, or patterns to assist the user in measuring distance, applying the device correctly, for aesthetics, etc. The external sliding member 32 may comprise a single or multiple apertures to aid in visualization of the internal sliding member 30, or for aesthetic purposes. The external sliding member 32 may traverse, or may be incorporated into the fixated ends 14.

The fixated ends 14 may comprise various shapes including, but not limited to, round, oval, square, rectangular, triangular, hexagonal, etc. The fixated ends 14 may comprise various lengths and sizes for accommodating differently sized users and/or differently sized body parts. The fixated ends 14 may be of various flexible, semi-rigid, or rigid materials including, but not limited to: plastic, foam, paper, cardboard, fabric, rubber, carbon fiber, fiberglass, leather, synthetic fiber, metal, etc. Further, the fixated ends 14 may comprise one or multiple layers of flexible, semi-rigid, or rigid materials, or any combination of said materials while still meeting the intended function of the embodiment. Additionally, the fixated ends 14 may have a tab portion to assist in the application or removal of said fixated ends 14. The fixated ends 14 may comprise various modes for attachment to the user including adhesive glues, wet or dry gels, suction, strapping, or incorporation into a garment, etc. for example. The fixated ends 14 may contain electrical contacts for the connection of the electronic connection cable 16, or components for the transmission of a wireless signal to the electronic console 20. Further, the contacts or wireless components may be external or internal of the materials comprising said fixated ends 14. The fixated ends 14 may comprise a mechanism for attachment or removal from the centralized linear regulator 22 such as using adhesive materials, rivets, heat pressing, sewing, button snaps, Velcro, clips or other suitable attachment mechanisms or methods. Further, the fixated ends 14 may comprise various color schemes, numbering sequences, or patterns to assist the user in measuring distance, applying the device correctly, for aesthetics, etc. The fixated ends 14 may have a single or multiple apertures to allow for visualization of skin during application, breathability of the material, aesthetics purposes, etc. The fixated ends 14 may be overlapped by either or both of the internal sliding member 30 or external sliding member 32 of the centralized linear regulator 22.

Figure 3:
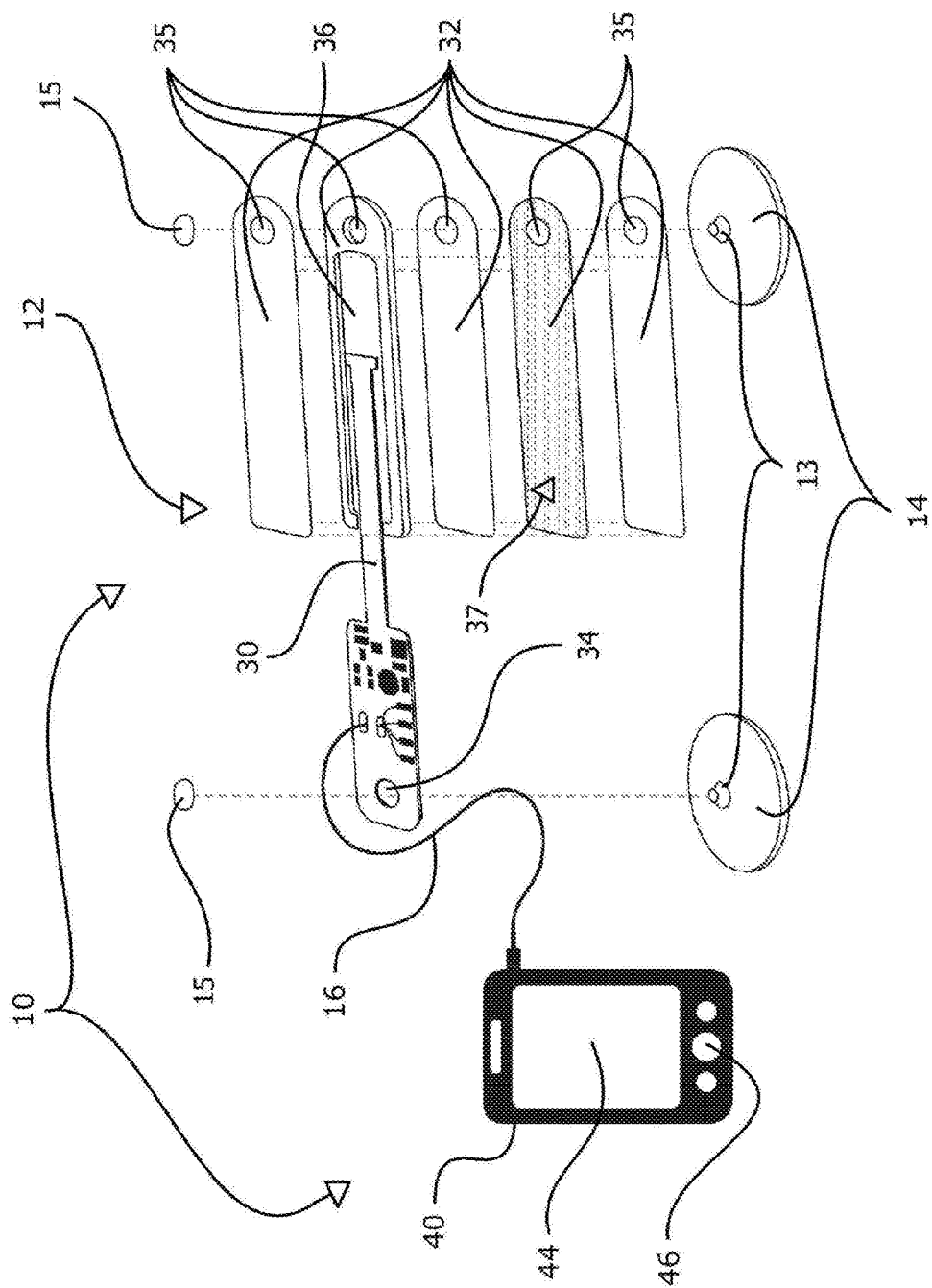
FIG. 3 illustrates a partially exploded perspective cross-sectional view of a linear sensing unit according to one embodiment of the present disclosure.

Turning to FIG. 3, a perspective view of a posture monitoring device 10 with electronic console 20, hardwire connection cable 16, and an exploded view of one possible embodiment of the sensing unit 12 and fixated ends 14 is depicted. The sensing unit 12 may comprise a centralized linear regulator 22 which may comprise an internal sliding member 30 and an external sliding member 32, a hardwire connection cable 16, and two fixated ends 14. The fixated ends 14 may comprise a button 13 with a securing member 15 traversing an aperture 34 of the internal sliding member 30 and a sliding channel 35 of the external sliding member 32 as a way to attach or remove the external sliding member from the sensing unit 12. The external sliding member 32 may comprise multiple layers, including a sliding channel 36 which may accept the internal sliding member 30, and a conductive layer 37 which may achieve the effect of a regulator with the internal sliding member 30. The centralized linear regulator 22 may be configured such that the internal sliding member 30 may traverse the sliding channel 36 of the external sliding member 32 which may allow for telescopic movement that may measure a change in distance between the two fixated ends 14. The internal sliding member 30 of the centralized linear regulator 22 may comprise a barbed or bulbous end 33 which may prevent said internal sliding member 30 from exiting the sliding channel 35 of the external sliding member 32.

Alternate embodiments of the sensing unit 12 may include variations to the centralized linear regulator 22 with internal sliding member 30 and external sliding member 32, and fixated ends 14.

The internal sliding member 30 of the linear regulator 22 may comprise a gradient concentration of conductive material along the length of the internal sliding member 30 which may assist with accuracy of measuring the electrical potential. The internal sliding member 30 may comprise one or more layers that may include both conductive and non-conductive materials including but not limited to: plastic, paper, cardboard, foam, fabric, leather, metal, elastic fabric, rubberized material, carbon fiber, fiberglass, electrolytes, semi-conducting materials, conducting materials, plasmas, magnetic substances, or other materials while still meeting the intended function of the embodiment. The barbed or bulbous end 33 of the internal sliding member 30 may comprise various widths, thicknesses, and shapes including, but not limited to: rectangular, square, round, oval, trapezoidal, or other shapes and/or combinations thereof while still meeting the intended function of the embodiment. The aperture 34 of the internal sliding member 30 may comprise various widths and shapes while still meeting the intended function of the embodiment. Further, the aperture 34 of the internal sliding member 30 may comprise a securing member 15 in order to assist with connecting or disconnecting the centralized linear regulator 22 to the fixated ends 14. The securing member 15 may comprise various materials including, but not limited to: metal, plastic, wood, Velcro, other materials, and/or combinations thereof while still meeting the intended function of the embodiment.

The external sliding member 32 of the linear regulator 22 may comprise a gradient concentration of conductive material which may change along the length of the external sliding member 32 to assist with accuracy of measuring the electrical potential. The external sliding member 32 may comprise one or more layers that may include both conductive and non-conductive materials including, but not limited to: plastic, paper, cardboard, foam, fabric, leather, metal, elastic fabric, rubberized material, carbon fiber, fiberglass, electrolytes, semi-conducting materials, conducting materials, plasmas, magnetic substances, or other materials while still meeting the intended function of the embodiment. The conductive layer 37 of the external sliding member 32 may be a separate layer or may be incorporated into another layer of the external sliding member 32. The conductive layer 37 may comprise various thicknesses, lengths, or shapes including, but not limited to: rectangular, round, square, oval, triangular, tubular, or a combination of shapes while still meeting the intended function of the embodiment. Further, the conductive layer 37 may comprise various gradient concentrations of conductive material along the length of the external sliding member 32 while still meeting the intended function of the embodiment. The sliding channel 36 of the external sliding member 32 may comprise various lengths, widths, and shapes including, but not limited to: rectangular tubular, square tubular, oval tubular, or combinations of shapes while still meeting the intended function of the embodiment. The sliding channel 36 may be coated with various lubricants to supplement sliding characteristics including, but not limited to: oils, silicone, synthetic lubricants, other lubricants, and/or combinations thereof. Further, the sliding channel 36 may comprise various textures including, but not limited to: smooth, grainy, undulated, dimpled, other textures, or a combination thereof while still meeting the intended function of the embodiment. Further, the aperture 34 of the external sliding member 32 may comprise a securing member 15 to assist with connecting or disconnecting the centralized linear regulator 22 to the fixated ends 14. The securing member 15 may comprise various materials including, but not limited to: metal, plastic, wood, Velcro, or other material and/or combinations thereof while still meeting the intended function of the embodiment.

Turning to FIG. 4, a perspective view of a posture monitoring device 10 being applied to a human back is depicted. The sensing unit 12 may comprise circular shaped fixated ends 14, and a hardwire connection cable 16 for communication with an electronic console 20. Alternatively, the sensing unit 12 may communicate to the electronic console 20 through a wireless transmission sending unit 18 as depicted in FIG. 2.

With respect to FIG. 5, a perspective view of the postural feedback device 10 being applied to more than one areas of a human back using multiple sensing units 12 is depicted. Alternatively, the sensing units may be placed onto any area of a human or animal body and may be placed on different body parts simultaneously. The electronic console 20 may be programmed to read the data supplied by each sensing unit 12 collectively or separately. The sensing units 12 may be connected to an electronic console 20 by one or multiple hardwire connection cables 16, using one or multiple connection jacks 52, or alternatively, a wireless transmission sending unit 18 as depicted in FIG. 2.

Turning to FIG. 6, a perspective view of a posture monitoring device 10 being used on the lumbar spine of a weightlifter to monitor spine position during a squat motion is depicted. The sensing unit 12 may comprise circular shaped fixated ends 14 and a hardwire connection cable 16 for communication with an electronic console 20. Alternatively, the sensing unit 12 may communicate with the electronic console 20 via using a wireless transmission sending unit 18 as depicted in FIG. 2.

Figure 7:
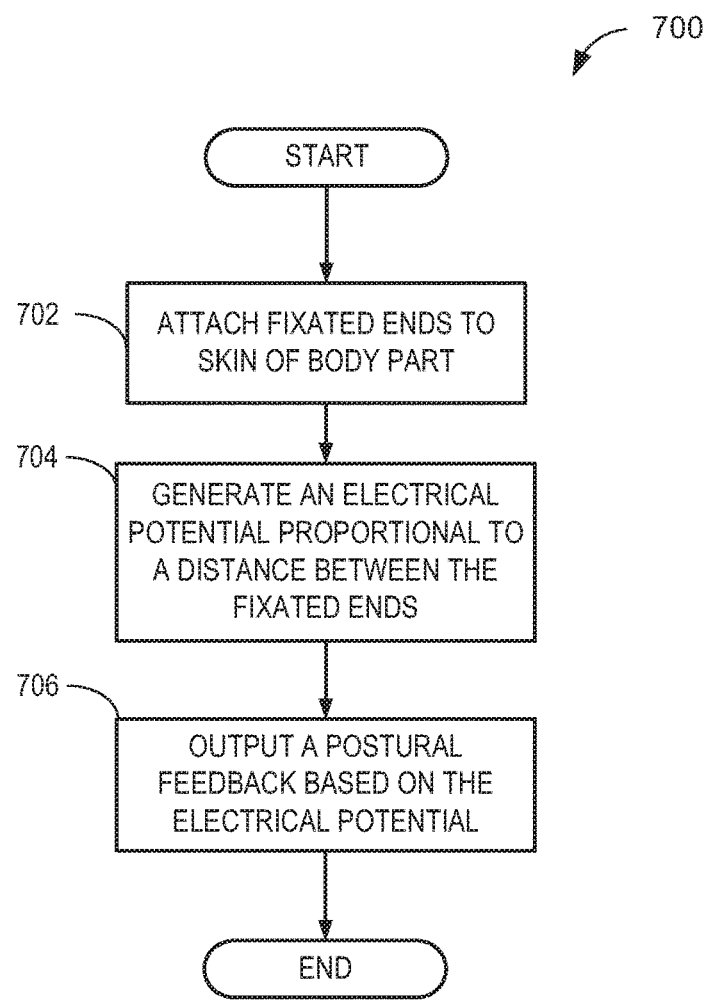
FIG. 7 illustrates a method of providing postural feedback to a user according to an embodiment of the present disclosure.

FIG. 7 illustrates a method 700 for providing postural feedback to a user via a postural feedback device. As illustrated, at step 702, the method 700 may include attaching one or more fixated ends of the postural feedback device to skin of a body part. The one or more fixated ends may be removably attached such that movement of the body part may change a distance between the one or more fixated ends. In some embodiments, the fixated ends may be removably attached to the skin, incorporated into a garment, or any combination thereof.

Upon movement of the body part, the method 700 may include at 704 generating an electrical potential with the centralized regulator. The electrical potential generated by the centralized regulator may be proportional to the distance between the one or more fixated ends. The electrical potential may be outputted by the centralized regulator to an electronic console for processing as described above.

At step 706, the method 700 may include outputting a feedback stimulus based upon the electrical potential. The feedback stimulus may be one or more of an audible stimulus, visual stimulus, tactile stimulus, vibratory stimulus, or any other suitable stimulus, notification, or presentation of postural feedback to the user.

Thus a postural feedback system is described that allows a user to monitor the alignment of various joints, muscles, or body parts by measuring changes in distance between at least two fixated points using a low profile, fixated, sensing unit. The device may provide information to the user via various electronic devices such as cell phones, pagers, bracelets, watches, etc. The information from the regulator may be transmitted to the electronic device by an electronic wire or wireless signal, and the electronic device may provide feedback to the user via tactile, auditory, visual, or other stimuli. The sensing unit has the advantage of being low profile and light-weight, allowing application on the user's skin via adhesion, strapping, incorporated into a garment, etc., while still being worn discreetly underneath clothing and without interfering with daily activities. It is to be understood that the disclosure is not limited to the embodiments described above, but encompasses any and all the embodiments within the scope of the claims.

As described above, for illustration purposes and not as a limitation, a postural feedback unit is disclosed with sensing unit comprising a centralized linear regulator with internal and external sliding members positioned between two fixated ends, a hardwire connection cable or wireless transmission sending unit, and electronic console. The linear regulator may comprise at least one internal and external sliding member which traverse each other, causing a measurable change in electrical potential that can be used to decipher a measurable change in distance. When applied to the user's skin over a desired area of measurement, changes in joint or muscle position result in variations in position of the internal sliding member on the external sliding member, thus a change in electrical potential, which can then be relayed to the electronic console and interpreted through various forms of stimuli to the user.

As one example, a postural feedback device may comprise one or more fixated ends, wherein at least one of the one or more fixated ends is removably attached to a body part of a user such that a change in position of the body part changes a distance between the one or more fixated ends. The postural feedback device may further comprise a sensing unit comprising a centralized regulator attached to the one or more fixated ends. The sensing unit may be configured to output an electrical potential proportional to the distance between the one or more fixated ends. Further, the postural feedback device may additionally comprise an electronic console which may be configured to receive the electrical potential from the centralized regulator and output a postural feedback to the user based upon the received electrical potential.

In some examples, the centralized linear regulator may be substituted with a rotary regulator comprising at least one actuator arm. Changes in distance between the two fixated ends may result in the actuator arm(s) turning the rotary regulator and the electrical potential measuring said change in distance, which can then be relayed to the electronic console and interpreted through various forms of stimuli to the user.

In further examples, the electronic console may comprise various wearable devices including wristwatches, bracelets, belts, pagers, cell phones, etc., while still being able to provide biofeedback stimuli to the user in the form of auditory, visual, tactile, or other stimulus.

It is to be understood that the configurations and/or approaches described herein are exemplary in nature, and that these specific embodiments or examples are not to be considered in a limiting sense, because numerous variations are possible. The subject matter of the present disclosure includes all novel and nonobvious combinations and sub-combinations of the various configurations, and other features, functions, and/or properties disclosed herein.

The invention claimed is:

1. A postural feedback device comprising:
one or more fixated ends, wherein at least one of the one or more fixated ends is removably attached to a body part of a user such that a change in a position of the body part changes a distance between the one or more fixated ends;
a sensing unit comprising a centralized regulator attached to the one or more fixated ends and configured to output an electrical potential proportional to the distance between the one or more fixated ends; and
an electronic console;
wherein the electronic console is configured to receive the electrical potential from the centralized regulator and output postural feedback to the user based upon the electrical potential, and
wherein the centralized regulator is a centralized linear potentiometer comprising an internal sliding member and an external sliding member, wherein at least one of the internal sliding member and the external sliding member is attached to the one or more fixated ends such that sliding of the internal sliding member on the external sliding member generates the electrical potential proportional to the distance between the one or more fixated ends.

2. The postural feedback device of claim 1, further comprising two or more centralized regulators.

3. The postural feedback device of claim 1, wherein at least one of the one or more fixated ends is removably attached to skin of the body part of the user by one or more of an adhesive mechanism, an adhesive material, and strapping.

4. The postural feedback device of claim 1, wherein the one or more fixated ends are incorporated into a garment for securing the sensing unit to skin of the body part of the user.

5. The postural feedback device of claim 1, wherein the postural feedback is one or more of an auditory stimulus, a visual stimulus, a tactile stimulus, and a vibratory stimulus.

6. The postural feedback device of claim 1, further comprising a wireless transmission sending unit configured to send a signal indicating an electrical gradient from the centralized regulator to the electronic console.

7. The postural feedback device of claim 1, wherein the centralized regulator comprises a capacitor.

8. A postural feedback device comprising:
one or more fixated ends, wherein at least one of the one or more fixated ends is removably attached to a body part of a user such that a change in a position of the body part changes a distance between the one or more fixated ends;
a sensing unit comprising one or more centralized regulators attached to the one or more fixated ends and configured to output an electrical potential proportional to the distance between the one or more fixated ends; and
an electronic console;
wherein the electronic console is configured to receive the electrical potential from the one or more centralized regulators and output postural feedback to the user, and
wherein the one or more centralized regulators comprise centralized rotary potentiometers; and
an actuator arm configured to attach to a fixated end of the one or more fixated ends and a centralized rotary potentiometer of the one or more centralized potentiometers, such that, upon a change in the distance between the one or more fixated ends, the actuator arm rotates the centralized rotary potentiometer, generating the electrical potential proportional to the distance between the fixated ends.

9. The postural feedback device of claim 8, wherein at least one of the one or more fixated ends is removably attached to skin of the body part of the user by an adhesive material.

10. The postural feedback device of claim 8, wherein at least one of the one or more fixated ends is removably attached to skin of the body part of the user by one or more of an adhesive mechanism, an adhesive material, and strapping, and is incorporated into a garment.

11. The postural feedback device of claim 8, wherein the postural feedback is one or more of an auditory stimulus, a visual stimulus, a tactile stimulus, and a vibratory stimulus.

12. The postural feedback device of claim 8, further comprising a wireless transmission sending unit configured to transmit a signal proportional to an electrical gradient from the one or more centralized regulators to the electronic console.

13. The postural feedback device of claim 8, wherein the one or more centralized regulators comprise capacitors.

14. A postural feedback device comprising:
one or more fixated ends, wherein at least one of the one or more fixated ends is removably attached to a body part of a user such that a change in a position of the body part changes a distance between the one or more fixated ends;
a sensing unit comprising one or more centralized regulators attached to the one or more fixated ends and configured to output an electrical potential proportional to the distance between the one or more fixated ends;
an electronic console;
wherein the electronic console is configured to receive the electrical potential from the one or more centralized regulators and output postural feedback to the user, and
wherein the one or more centralized regulators comprise centralized rotary potentiometers; and two or more actuator arms, each of the two or more actuator arms attached to a fixated end of the one or more fixated ends and a centralized rotary potentiometer of the one or more centralized regulators, such that, upon a change in the distance between the one or more fixated ends, each of the two or more actuator arms rotates the centralized rotary potentiometer, generating the electrical potential proportional to the distance between the fixated ends.

15. The postural feedback device of claim 14, wherein at least one of the one or more fixated ends is removably attached to skin of the body part of the user by an adhesive material.

16. The postural feedback device of claim 14, wherein the one or more fixated ends are incorporated into a garment for securing the sensing unit to skin of the body part of the user.

17. The postural feedback device of claim 14, wherein the postural feedback is one or more of an auditory stimulus, a visual stimulus, a tactile stimulus, and a vibratory stimulus.

18. The postural feedback device of claim 14, further comprising a wireless transmission sending unit configured to send a signal indicating an electrical gradient from the one or more centralized regulators to the electronic console.

19. The postural feedback device of claim 14, wherein the one or more centralized regulators comprise capacitors.

20. The postural feedback device of claim 1, wherein at least one of the one or more fixated ends is removably attached to skin of the body part of the user by an adhesive material.

* * * * *